United States Patent
Rothen-Weinhold et al.

(10) Patent No.: US 6,245,346 B1
(45) Date of Patent: Jun. 12, 2001

(54) PHARMACEUTICAL COMPOSITIONS FOR THE SUSTAINED RELEASE OF INSOLUBLE ACTIVE PRINCIPLES

(75) Inventors: Alexandra Rothen-Weinhold, Croix-De-Rozon; Robert Gurny, Geneva; Piero Orsolini, Martigny; Frédéric Heimgartner, Villeneuve, all of (CH)

(73) Assignee: Debio Recherche Pharmaceutique S.A. (FR)

( * ) Notice: Subject to any disclaimer, the term of this patent is extended or adjusted under 35 U.S.C. 154(b) by 0 days.

(21) Appl. No.: 09/180,451

(22) PCT Filed: Apr. 28, 1997

(86) PCT No.: PCT/EP97/02187

§ 371 Date: Jan. 6, 1999

§ 102(e) Date: Jan. 6, 1999

(87) PCT Pub. No.: WO97/41836

PCT Pub. Date: Nov. 13, 1997

(30) Foreign Application Priority Data

May 6, 1996 (FR) .................................... 96 05630

(51) Int. Cl.[7] .................................................. A61F 2/00
(52) U.S. Cl. .................... 424/426; 424/423; 424/486; 424/489
(58) Field of Search ................................. 424/489, 426, 424/423, 486, 485

(56) References Cited

U.S. PATENT DOCUMENTS

| | | |
|---|---|---|
| 3,773,919 | 11/1973 | Boswell et al. . |
| 4,622,244 | 11/1986 | Lapka et al. . |
| 5,869,079 | * 2/1999 | Wong et al. .......................... 424/426 |

FOREIGN PATENT DOCUMENTS

| | | |
|---|---|---|
| 679207 | 1/1992 | (CH) . |
| 0 474 098 A | 3/1992 | (EP) . |
| 0 669 128 A | 8/1995 | (EP) . |
| 2 620 621 A | 3/1989 | (FR) . |
| 2 246 514 A | 2/1992 | (GB) . |
| WO 96 10397 | 4/1996 | (WO) . |

OTHER PUBLICATIONS

Journal of Controlled release, vol. 31, No. 1 Aug. 1, 1994, pp. 33–39.
Journal of Controlled release, vol, 23, No. 1, Jan. 1, 1993, pp. 55–63.

* cited by examiner

Primary Examiner—Thurman K. Page
Assistant Examiner—Charesse L. Evans
(74) Attorney, Agent, or Firm—Piper Marbury Rudnick & Wolfe

(57) ABSTRACT

Pharmaceutical composition for the controlled release of at least one water-insoluble active principle, containing a homopolymer of D,L-lactic acid or of L-lactic acid of low molecular weight combined with said active principle, wherein the molecular weight of the homopolymer of D,L-lactic acid is between approximately 2,000 and 6,000 daltons or the molecular weight of the homopolymer of L-lactic acid is about 4,000 daltons.

38 Claims, 2 Drawing Sheets

Figure 1:
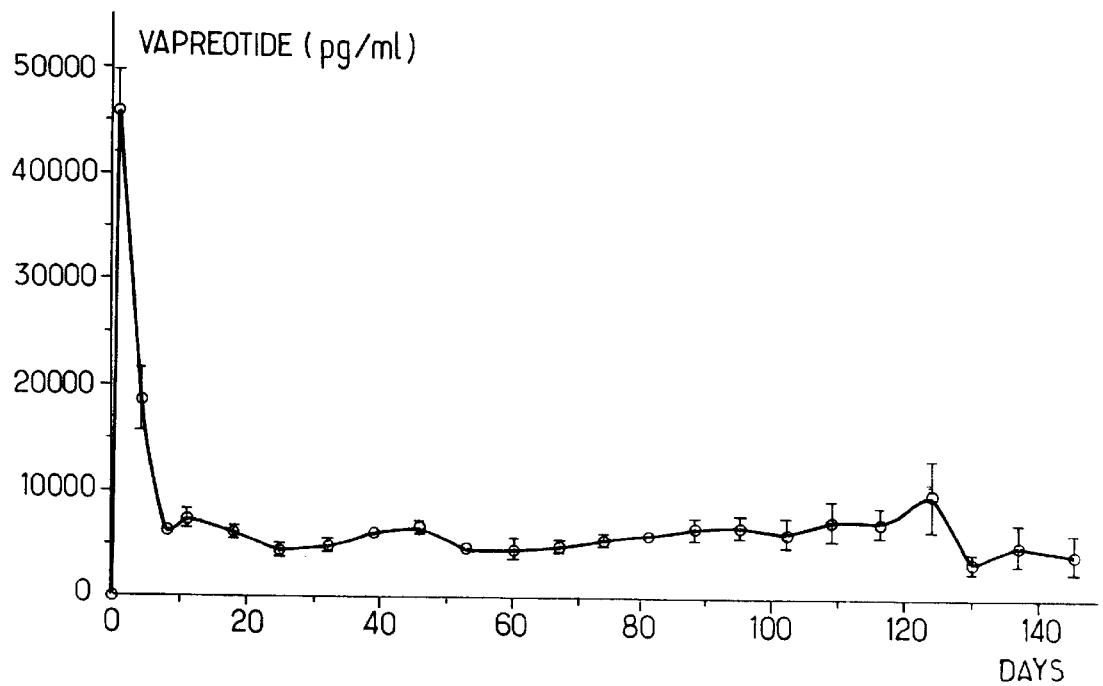

PHARMACEUTICAL COMPOSITIONS FOR THE SUSTAINED RELEASE OF INSOLUBLE ACTIVE PRINCIPLES

The present invention relates to pharmaceutical compositions containing biodegradable polymers for the controlled release of water-insoluble active principles.

Pharmaceutical compositions for controlled release containing biodegradable polymers are extremely useful for the distribution of medical and pharmaceutical products and find a great variety of applications in which they offer numerous advantages in relation to formulations of standard medicines.

Simple administration of a formulation for controlled release assures slow release of the active principle in the course of a sustained period.

One of the first applications of this type of formulation for controlled release is in the domain of drug abuse. The treatment of patients who are addicted to the use of drugs is made delicate and difficult insofar as, with standard formulations, it is not always easy to obtain the co-operation of the patient. Thus, with standard formulations, there is always the risk that the patient refuses to follow the necessary treatment at the desired moment. With formulations for controlled release, a single dose assures on the other hand effective treatment for a certain length of time, longer than what it is possible to obtain with a single dose.

The formulations for controlled release are equally particularly useful in applications such as cancer therapy where long term treatments are often necessary.

Another important application of these formulations is in the field of hormone therapy for example in connection with contraceptives where continuous release of the active principle at a relatively constant concentration is necessary for a certain length of time.

Pharmaceutical compositions for controlled release can thus be proposed in a variety of galenical formulations. Thus there are implant formulations, as well as formulations which allow oral or parenteral administration. Oral formulations are normally presented in the form of tablets or capsules which can be easily swallowed or ingested.

Parenteral formulations can be presented notably in the form of microgranules, microspheres or microcapsules.

According to the aim and the circumstances of the desired form of therapy, implants can sometimes be preferred to parenteral formulations. This preference exists notably in a case where it is desired to have a certain flexibility in relation to the therapy protocol. In relation to parenteral formulations, implants present the advantage of being able to be removed surgically, if it should be necessary for any reason, to stop the treatment before the complete release of the active principle has taken place.

The pharmaceutical compositions according to the present invention can be presented notably in the form of implants, microgranules and/or microspheres.

The discovery of polymers which are easily biodegradable has considerably advanced the technology of the field of pharmaceutical compositions for controlled release. It is of course advantageous to be able to introduce a pharmaceutical composition containing polymer into the human or animal body knowing that the polymer is going to degrade in the course of a certain lapse of time, thus permitting slow release of the active principle without letting any foreign matter remain in the patient's body.

As far as biodegradable polymers are concerned the copolymers and homopolymers of polylactide and polyglycolide are particularly preferred in the formulations for controlled release because they are easily degradable, decomposing into inoffensive products such carbon dioxide and water, and not leaving any residue in the time after the release of the active principle.

The U.S. Pat. No. 3,773,919 describes polymer formulations of medicines containing polylactides. It is mentioned there that the invention presents a particular interest for medicines which require prolonged administration or sustained slow release, for example for certain medicines for regulating fertility or the hormones used in hormone substitution therapy.

It is advisable to notice that implants, such as microgranules, can be prepared according to a "dry process" which avoids the use of solvents for the prior dissolution of the active principles and/or of the polymers. This avoids the drawback of processes such as microencapsulation, where the problem is always encountered of traces of residual solvent which can compromise the use of the compositions for therapeutic purposes. The Applicant Company has perfected this "dry process" for the preparation of microgranules and implants. This process has been described in the Swiss patent 679 207 of which the Applicant Company is the owner. Microgranules coming from this process permit regular release of the active substance over a period of approximately one month.

However, there still exists a need for pharmaceutical compositions which permit sustained release of water-insoluble active principles over a more significant length of time such as two or even three or four months.

Now, in a way that has been totally surprising and unexpected, the Applicant Company has been able to perfect a new type of pharmaceutical composition which permits controlled release of water-insoluble active principles over a period longer than one month, and in particular of two to three months, or even longer.

The pharmaceutical compositions according to the present invention are characterised by the fact that they include a homopolymer of lactic acid with a low molecular weight.

The polymer can be a homopolymer of D,L-lactic acid or of L-lactic acid. The Applicant Company has discovered that the use of this polymer makes it possible to obtain slow and regular release of an active principle during two to three months, or even longer.

This result is even more surprising in that the polymer used in the present case is a polymer which has a low molecular weight. In fact, one might think that the lower the molecular weight of the polymer, the more significant would be its speed of degradation. The Applicant Company discovered, however, that this was not so for the homopolymers of D,L-lactic acid and of L-lactic acid.

In practice, the molecular weight of the homopolymer of L-lactic acid is advantageously chosen to be between approximately 1,000 and 30,000, preferably between approximately 3,000 and 15,000, and being even more preferably about 4,000.

The molecular weight of the homopolymer of D,L-lactic acid is advantageously chosen to be between approximately 1,000 and 30,000, preferably between approximately 2,000 and 20,000 and even more preferably between approximately 2,000 and 6,000.

The percentage of polymer in the pharmaceutical composition according to the invention is between 98 and 70%, preferably between 95 and 75% and even more preferably between 85 and 75%.

The use of this type of polymer thus makes it possible to obtain slow and progressive release of the active principles which have been made water-insoluble.

According to the invention, "water-insoluble active principles" are understood to be active principles which can themselves be soluble in an aqueous solution but which are rendered insoluble by being transformed into an insoluble salt of the active principle.

In the context of the present invention, "water-insoluble" is understood to mean a solubility in water which does not exceed 100 µg/ml (definition by the USP, United States Pharmacopoea) in conditions of ambient temperature and slow agitation.

The active principle made water-insoluble according to the present invention can be chosen amongst proteins, polypeptides, hormones. In particular, the active principle can be chosen amongst the acceptable pharmaceutical salts of oxytocin, vasopressin, ACTH, calcitonin, LH-RH or its analogues, the epidermal growth factor, prolactin, inhibin, interferon, somatostatin, or its analogues such as vapreotide pamoate, insulin, glucagon, the atrial natriuretic factor, endorphin, a peptic inhibitor of renin, growth hormone releasing factor, the peptide T as well as their synthetic analogues.

The pharmaceutically acceptable insoluble salts of the active principle can be advantageously chosen from pamoate, tannate, stearate or palmitate.

The present invention thus concerns a pharmaceutical composition for the controlled release of at least one water-insoluble active principle, comprising a homopolymer of D,L-lactic acid or of L-lactic acid having a low molecular weight and being closely associated with said active principle.

The pharmaceutical compositions according to the invention can present themselves in the form of implants, microgranules or microspheres.

The implants and the microgranules according to the invention can be prepared according to known methods, notably the one which is described in the Swiss patent 679 207.

Thus the active principle and the polymer, both in pulverulent form, are mixed when dry in an appropriate apparatus, such as a ball mill, at the ambient temperature (about 25° C.) or even at a lower temperature, for example 5–10° C.

Once the mixture has been duly homogenised, it is subjected to progressive compression and simultaneously to progressive heating before being extruded.

The mixture that has thus been pre-compressed and pre-heated is then subjected to extrusion, at a temperature most usually of between approximately 80 and 100° C. The extrusion can take place under a pressure varying between 50 and 500 kg/cm$^2$.

The threads thus extruded are cooled then cut into short sticks or other forms as far as the implants are concerned.

An alternative method of preparing the implants according to the invention is described in Example 1.

As far as the microgranules are concerned, the extrusion product is cooled and then pulverised at a low temperature, of between 0 and –30° C. The microgranules can then be sorted according to their dimensions.

Within the framework of the present invention, the size of the microgranules is advantageously around 15 µm The microspheres according to the present invention can be prepared according to the method described in the U.S. Pat. No. 3,773,919, amongst others.

According to this patent, the active principle is dispersed in a polymer solution in an organic solvent. An agent which is incompatible with the polymer solvent system is added, the temperature and the pressure are then varied. This causes a phenomenon which is called "coacervation" i.e. the precipitation of the polymer with the dispersed active principle, which produces microspheres which consist of a matrix of polymer in which the molecules of the active principle are dispersed. The microspheres thus obtained are separated by filtration then dried.

The size of the microspheres according to the invention is advantageously around 40 µm.

According to an advantageous embodiment of the invention, the percentage of the active principle in relation to the total weight is between approximately 1 and 45%, preferably between approximately 5 and 10% if it is a question of microgranules or microspheres, and between approximately 2 and 30%, preferably between approximately 5 and 25% and even more preferably between approximately 15 and 25% if it is a question of implants.

According to a particularly preferred form of embodiment of the invention, an effective quantity of the active principle is released during a period of at least one month, preferably of at least two months, and even more preferably of more than three months.

The profiles of release according to the invention can show a "burst effect" i.e. an immediate significant release, followed by a slow and regular release over a long period.

Figure 2:
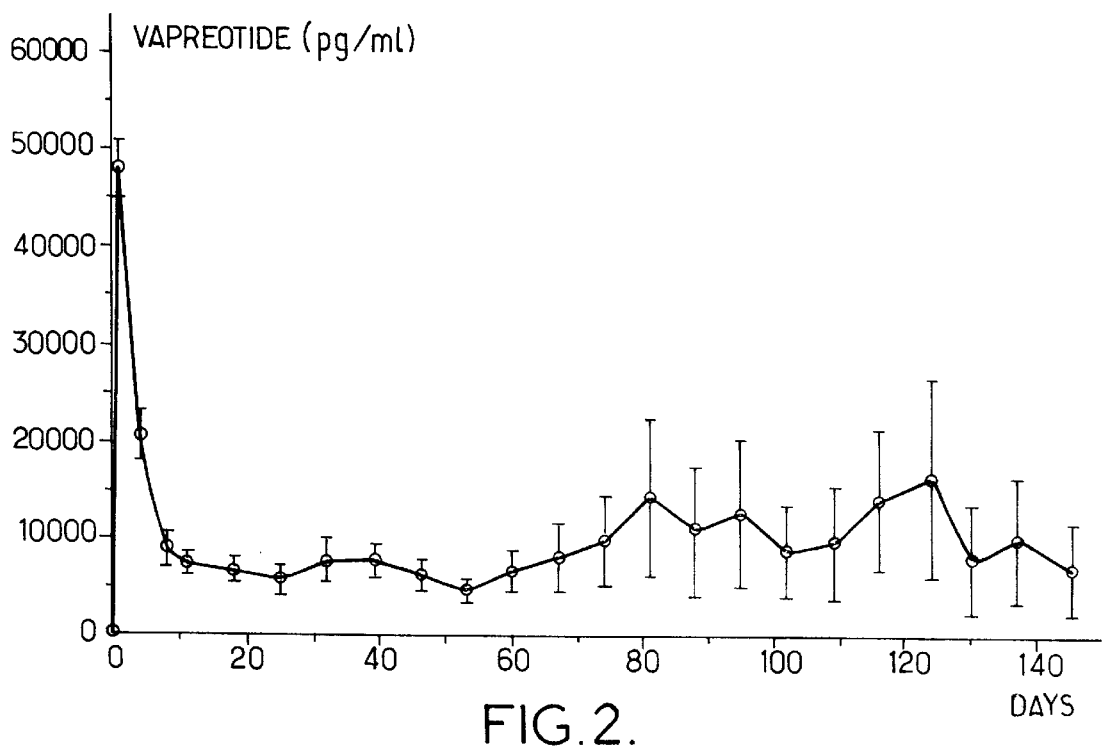
Figure 3:
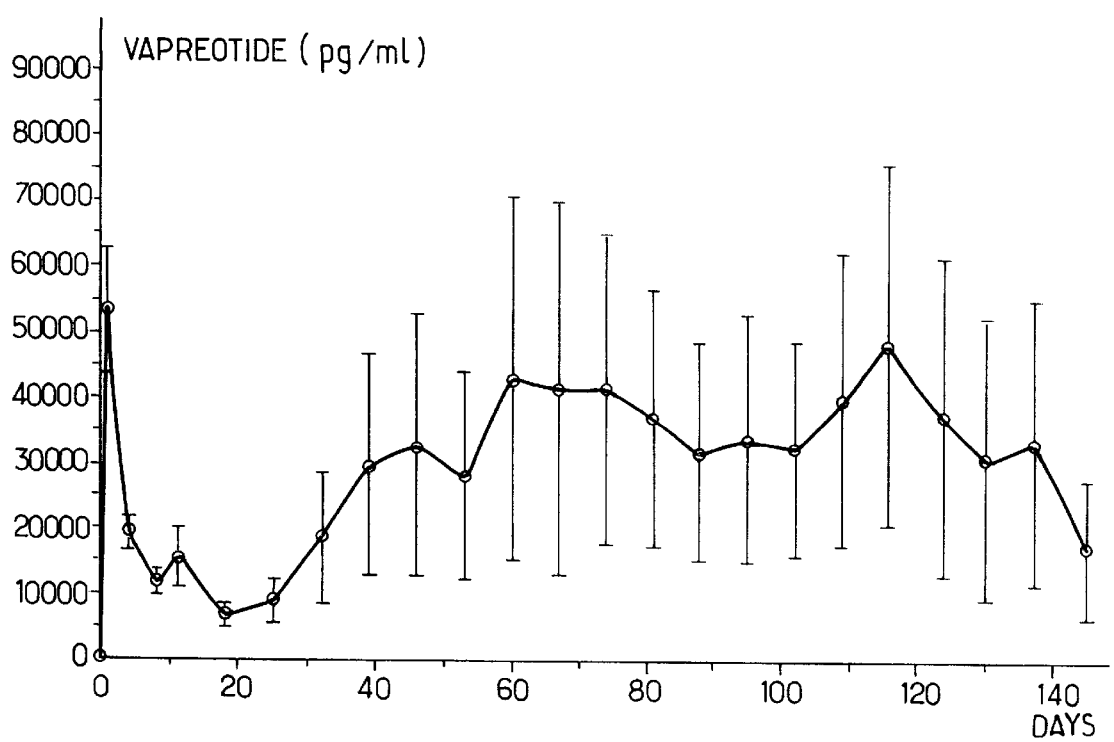

FIGS. 1, 2 and 3 show profiles of release obtained from implants according to the invention with different percentages of active principle.

The examples which follow are intended to better illustrate particular aspects of the invention but cannot in any way be considered as restrictive.

EXAMPLE 1

With the aid of a three-dimensional mixer, a polymer called L104, which is an L-polylactic acid having a molecular mass of approximately 4,000 and is marketed by the company BOEHRINGER INGELHEIM, is mixed with vapreotide pamoate (an analogue of somatostatin sold by NOVA BIOCHEM in Switzerland).

The mixture is homogenised in an agate mortar and then de-ionised.

The extrusion of the mixture obtained is carried out at a temperature of approximately 80° C. on a piston extruder.

The filament thus obtained is then divided up into cylindrical implants of 15 mm in length with the aid of a scalpel.

EXAMPLE 2

Preparation of Microgranules According to the Invention

The process is the same as in example 1 up to the obtaining of filaments which are cooled at the ambient temperature. Then they are cut into small portions and finally crushed at –30° C. After sieving, microgranules with an average dimension of 15 µm or less are collected.

The chemical analysis carried out on the samples of extruded and crushed product confirms the perfect homogeneity of the dispersion of the active substance within the copolymer mass.

EXAMPLE 3

Implantation in an Animal and Release Curve

Implants are prepared as in example 1 using percentages of active principle of 15, 20 and 25%. Each implant is sterilised by gamma radiation, with a dose of 2.5 M rads.

Each type of implant is then injected into the subcutaneous tissue of the skin of the neck of a male albino rat from the stock Spragne Dawleu, the rats being 8 to 9 weeks old and having an average weight of between 330 and 340 g. The injection is made by means of a trocar, the prototype of which is provided by S.F.M. in Germany.

Blood samples are then taken to determine, by RIA dosing, release of the active principle. FIGS. 1, 2 and 3 show the release curves for the different percentages of active principle (15, 20, and 25% respectively). It should be noted that sustained release is recorded beyond four months (120 days).

What is claimed is:

1. Pharmaceutical composition for the controlled release of at least one water-insoluble active principle, containing a hompolymer of D,L-lactic acid or of L-lactic acid of low molecular weight combined with said active principle, wherein the molecular weight of the hompolymer of D,L-lactic acid is between approximately 2,000 and 6,000 or the molecular weight of the homopolymer of L-lactic acid is about 4,000.

2. Pharmaceutical composition according to claim 1, wherein the percentage of polymer is between 98% and 70%.

3. Pharmaceutical composition according to claim 2, wherein the percentage of polymer is preferably between 95% and 75%.

4. Pharmaceutical composition according to claim 3, wherein the percentage of polymer is between 85% and 75%.

5. Pharmaceutical composition according to claim 1, wherein the water-insoluble active principle is selected from the group constituted by the pharmaceutically acceptable salts of oxytocin, vasopressin, ACTH, calcitonin, LH-RH or its analogues, the epidermal growth factor, prolactain, inhibin, interferon, somatostatin or one of its analogues such as Vapreotide, insulin, glucagon, the atrial natriuretic factor, endorphin, a peptic inhibitor of renin, growth hormone release factor, the peptide T as well as their synthetic analogues.

6. Pharmaceutical composition according to claim 1, wherein the pharmaceutically acceptable salts of the active principle are selected from the group constituted by pamoate, tannate, stearate and palmitate.

7. Pharmaceutical composition according to claim 1, wherein the active principle is vapreotide pamoate.

8. Pharmaceutical composition according to claim 1, wherein the percentage of the active principle in relation to the total weight is between approximately 1 and 45%.

9. Pharmaceutical composition according to claim 1 provided in the form of implants.

10. Pharmaceutical composition according to claim 1 provided in the form of microgranules.

11. Pharmaceutical composition according to claim 1 provided in the form of microspheres.

12. Pharmaceutical composition according to claim 1, wherein the percentage of the active principle in relation to the total weight is between approximately 2 and 30%.

13. Pharmaceutical composition according to claim 1, wherein the percentage of the active principle in relation to the total weight is between approximately 5 and 25%.

14. Pharmaceutical composition according to claim 13, wherein the percentage of the active principle in relation to the total weight is between approximately 15 and 25%.

15. Pharmaceutical composition according to claims 13 and 14, wherein the percentage of the active principle in relation to the total weight is between approximately 1 and 45%.

16. Pharmaceutical composition according to claim 15, wherein the percentage of the active principle in relation to the total weight is between approximately 5 and 10%.

17. Pharmaceutical composition according to claim 1, wherein an effective quantity of the active principle is released during a period of at least one month.

18. Pharmaceutical composition according to claim 17, wherein an effective quantity of the active principle is released during a period of at least two months.

19. Pharmaceutical composition according to claim 18, wherein the effective quantity of the active principle is released during a period of more than three months.

20. Pharmaceutical composition for the controlled release of at least one water-insoluble active principle, containing a homopolymer of L-lactic acid of low molecular weight combined with said active principle, wherein the molecular weight of the homopolymer of L-lactic acid is about 4,000 daltons.

21. Pharmaceutical composition according to claim 20, wherein the percentage of polymer is between 98% and 70%.

22. Pharmaceutical composition according to claim 21, wherein the percentage of polymer is preferably between 95% and 75%.

23. Pharmaceutical composition according to claim 22, wherein the percentage of polymer is between 85% and 75%.

24. Pharmaceutical composition according to claim 20, wherein the water-insoluble active principle is selected from the group constituted by the pharmaceutically acceptable salts of oxytocin, vasopressin, ACTH, calcitonin, LH-RH or its analogues, the epidermal growth factor, prolactain, inhibin, interferon, somatostatin or one of its analogues such as Vapreotide, insulin, glucagon, the atrial natriuretic factor, endorphin, a peptic inhibitor of renin, growth hormone release factor, the peptide T as well as their synthetic analogues.

25. Pharmaceutical composition according to claim 20, wherein the pharmaceutically acceptable salts of the active principle are selected from the group constituted by pamoate, tannate, stearate and palmitate.

26. Pharmaceutical composition according to claim 20, wherein the active principle is vapreotide pamoate.

27. Pharmaceutical composition according to claim 26, wherein the percentage of the active principle in relation to the total weight is between approximately 1 and 45%.

28. Pharmaceutical composition according to claim 20 provided in the form of implants.

29. Pharmaceutical composition according to claim 20 provided in the form of microgranules.

30. Pharmaceutical composition according to claim 20 provided in the form of microspheres.

31. Pharmaceutical composition according to claim 20 wherein the percentage of the active principle in relation to the total weight is between approximately 2 and 30%.

32. Pharmaceutical composition according to claim 20, wherein the percentage of the active principle in relation to the total weight is between approximately 5 and 25%.

33. Pharmaceutical composition according to claim 32, wherein the percentage of the active principle in relation to the total weight is between approximately 15 and 25%.

34. Pharmaceutical composition according to claims 32 and 33 wherein the percentage of the active principle in relation to the total weight is between approximately 1 and 45%.

35. Pharmaceutical composition according to claim 34, wherein the percentage of the active principle in relation to the total weight is between approximately 5 and 10%.

36. Pharmaceutical composition according to claim 20, wherein an effective quantity of the active principle is released during a period of at least one month.

37. Pharmaceutical composition according to claim 36, wherein an effective quantity of the active principle is released during a period of at least two months.

38. Pharmaceutical composition according to claim 37, wherein the effective quantity of the active principle is released during a period of more than three months.

* * * * *